United States Patent
Yu et al.

(10) Patent No.: US 7,867,709 B2
(45) Date of Patent: Jan. 11, 2011

(54) METHOD FOR DETECTING CANCER AND METHOD FOR SUPPRESSING CANCER

(75) Inventors: Wei Yu, Berkeley, CA (US); Johji Inazawa, Tokyo (JP); Issei Imoto, Tokyo (JP)

(73) Assignees: Fujifilm Corporation, Tokyo (JP); Tokyo Medical and Dental University, Tokyo (JP)

( * ) Notice: Subject to any disclaimer, the term of this patent is extended or adjusted under 35 U.S.C. 154(b) by 584 days.

(21) Appl. No.: 11/723,712

(22) Filed: Mar. 21, 2007

(65) Prior Publication Data

US 2007/0238119 A1  Oct. 11, 2007

(30) Foreign Application Priority Data

Mar. 22, 2006  (JP) .............................. 2006-078787

(51) Int. Cl.
*C12Q 1/68* (2006.01)
(52) U.S. Cl. .......................................................... 435/6
(58) Field of Classification Search ........................ None
See application file for complete search history.

(56) References Cited

U.S. PATENT DOCUMENTS

| 2005/0208500 A1 | 9/2005 | Erlander et al. |
| 2006/0003327 A1 | 1/2006 | Achiron et al. |
| 2007/0141066 A1* | 6/2007 | Phillips et al. ............ 424/155.1 |

FOREIGN PATENT DOCUMENTS

| WO | WO-2005/024055 A1 | 3/2005 |
| WO | WO-2005/118869 A2 | 12/2005 |
| WO | WO-2006/085746 A2 | 8/2006 |

OTHER PUBLICATIONS

Onda et al., Endocrine—Related Cancer, Dec. 2004, vol. 11, No. 4, pp. 843-854, XP-002434783, ISN: 1351-0088.
Wang et al., US National Library of Medicine (NLM), AN: NLM16778963, Jun. 18, 2006, XP-002445765.
Wang et al., Journal of Peking University Health Sciences, Jun. 18, 2006, vol. 38, No. 3, pp. 239-243, Abstract only.
Oriola et at., European Journal of Cancer, Dec. 2001, vol. 37, No. 18, pp. 2470-2474.
Liu et al, European Journal of Biochemistry, vol. 268, No. 12, Jun. 2001, pp. 3501-3512, XP-002434784.
Bauer et al., Science, vol. 201, Sep. 1978, pp. 1232-1233, XP-002434785.
Wang et al., Journal of Biomolecular Screening, vol. 11, No. 4, 2006, pp. 369-376, XP009084149.
Takaya et al.; Cellular and Molecular Biology 67, American Association for Cancer Research, vol. 48, Apr. 18, 2007, pp. 1245, Abstract No. 5263, XP-001536231.

* cited by examiner

*Primary Examiner*—James Martinell
(74) *Attorney, Agent, or Firm*—Birch, Stewart, Kolasch & Birch, LLP (57) ABSTRACT

An object of the present invention is to provide a method for detecting cancer through identification of genes exhibiting characteristic behavior in the cases of cancer such as anaplastic thyroid cancer. The present invention provides a method for detecting cancer which comprises detecting canceration of a specimen using the amplification of a gene of the p12 region of chromosome 8 in the specimen as an indicator.

3 Claims, 2 Drawing Sheets

SEQUENCE LISTING

```
<160> NUMBER OF SEQ ID NOS: 1

<210> SEQ ID NO 1
<211> LENGTH: 19
<212> TYPE: DNA
<213> ORGANISM: Homo sapiens

<400> SEQUENCE: 1
catcctttcc tcaatgtct                                                 19
```

METHOD FOR DETECTING CANCER AND METHOD FOR SUPPRESSING CANCER

TECHNICAL FIELD

The present invention relates to a method for detecting genome amplification in the p12 region of human chromosome 8 for early diagnosis of cancers such as anaplastic thyroid cancer and for examination of the malignancy of cancer such as anaplastic thyroid cancer. Furthermore, the present invention relates to a method for suppressing cancer growth using findings concerning the relationship between a novel amplified gene in thyroid anaplastic cancer 1 (NATA1) and anaplastic thyroid cancer.

BACKGROUND ART

Thyroid cancer is classified based on four tissue types: papillary cancer derived from follicular cells, follicular cancer, anaplastic carcinoma, and encephaloid carcinoma derived from parafollicular cells. Among thyroid cancers, anaplastic thyroid cancer (ATC) grows very rapidly, so that approximately 80% of anaplastic carcinoma patients die within 1 year even if treated (Passler, C., et al., Langenbecks. Arch. Surg. 384, 284-293, 1999; Voutilainen, P. E., et al., World. J. Surg. 23, 975-978, 1999). Therefore, treatment of anaplastic thyroid cancer is difficult. It is thus important to thoroughly treat differentiated thyroid cancer before anaplastic transformation. Accordingly, understanding of the development mechanism of anaplastic thyroid cancer and selection of differentiated thyroid cancer cases in which anaplastic transformation is likely to take place are required. Based on studies conducted to date, it is considered that gene alteration takes place successively like a chain reaction during the processes of cell differentiation and proliferation, resulting in canceration. However, the gene alteration that actually induces anaplastic thyroid cancer remains unknown. Therefore, there are currently no methods for detecting anaplastic thyroid cancer. Nor are there any methods for examining the malignancy of anaplastic thyroid cancer.

DISCLOSURE OF THE INVENTION

Successful elucidation of the mechanism of canceration of thyroid cells at the gene level will enable early detection of canceration of thyroid cells at the gene level and diagnosis of the malignancy of thyroid cancer. Furthermore, it will also enable establishment of methods for selecting and developing drugs, as well as therapeutic methods based on such mechanisms. Specifically, this object can be achieved by identifying genes exhibiting characteristic behavior observed in anaplastic thyroid cancer cases and then carrying out technical examination mainly targeting such genes. Hence, an object to be achieved by the present invention is to provide a method for detecting cancer through identification of genes exhibiting characteristic behavior in the cases of cancer such as anaplastic thyroid cancer.

Comparative Genomic Hybridization (CGH) is the best method for conveniently and rapidly analyzing genetic abnormalities accompanying amplification or deletion of numerous genes in the genome. To analyze genetic abnormalities in the genome involved in canceration and higher cancer malignancy, the present inventors have selected 800 types of BAC/PAC DNAs to be subjected to CGH assay (Takada H., et al., Cancer Sci. 96, 100-105, 2005). As a result, the present inventors have succeeded in identification of an oncogene that activates the canceration of thyroid cells; that is, a Novel Amplified gene in Thyroid Anaplastic cancer 1 (NATA1). Moreover, the present inventors have succeeded in discovering NATA1 gene amplification. Specifically, the present inventors have succeeded in discovering that increased NATA1 protein levels significantly promote the proliferation of anaplastic thyroid cancer cells and that suppression of the transcriptional products of the NATA1 gene results in significantly decreased levels of anaplastic thyroid cancer cell proliferation. Thus, the present inventors have completed the present invention.

Specifically, the present invention provides a method for detecting cancer which comprises detecting canceration of a specimen using the amplification of a gene of the p12 region of chromosome 8 in the specimen as an indicator.

Preferably, the above gene is a FUT10 gene, a LOC84549 gene, a FLJ23263 gene, an RNF122 gene, or a NATA1 gene.

Preferably, the value indicating the degree of such gene amplification is 1.5 or more times greater than that of a normal specimen.

Preferably, a specimen is a cell derived from the thyroid gland.

Preferably, cancer is anaplastic thyroid cancer.

Preferably, the method of the present invention is a method for detecting thyroid cancer, which comprises detecting canceration of thyroid cells using the amplification of NATA1 gene in the thyroid cells as an indicator.

Preferably, gene amplification is detected using a DNA chip method, a Southern blot method, a Northern blot method, a real-time RT-PCR method, a FISH method, a CGH method, or an array CGH method.

Another aspect of the present invention provides a method for suppressing cell proliferation, which comprises in vitro introduction of siRNA, shRNA, or an antisense oligonucleotide of a gene selected from the group consisting of a FUT10 gene, a LOC84549 gene, a FLJ23263 gene, an RNF122 gene, and a NATA1 gene into cells.

Still another aspect of the present invention provides a cell proliferation suppressing agent which comprises siRNA, shRNA, or an antisense oligonucleotide of a gene selected from the group consisting of the FUT10 gene, the LOC84549 gene, the FLJ23263 gene, the RNF122 gene, and the NATA1 gene.

Still another aspect of the present invention provides a method for activating cell proliferation which comprises in vitro introduction of a gene selected from the group consisting of the FUT10 gene, the LOC84549 gene, the FLJ23263 gene, the RNF122 gene, and the NATA1 gene into cells.

Still another aspect of the present invention provides a cell proliferation activating agent which comprises a gene selected from the group consisting of the FUT10 gene, the LOC84549 gene, the FLJ23263 gene, the RNF122 gene, and the NATA1 gene.

BRIEF DESCRIPTION OF THE INVENTION

A: CGH-array image (upper figure) and gene alteration (lower figure) of the entire chromosome of anaplastic thyroid cancer cells (8305C) are shown. Amplification of the copy number of PAC clone RP1-25D10 in the human 8p12 region can be confirmed with a clear green signal (log 2 ratio=3.2, red arrow)

B: FISH image is shown where BAC RP11-258M15 was used as a probe and hybridized to the metaphase chromosome of the 8305C cell line.

C: On the left, a map covering the 8p12 region amplified in anaplastic thyroid cancer cells is shown. BAC used for FISH is denoted with a vertical bar. All markers and transcriptional products match the corresponding data in the genome database. In the center, the results of analyzing the DNA copy numbers as determined by FISH are summarized. The horizontal axis (top) indicates the number of FISH signals determined with the use of each BAC probe (the number of signals less than 20 was discarded). On the right, the amplification position of 4 cell species was determined to be the 8p11-12 region that had been observed to be amplified in 3 different cancer types.

Overall line: Amplification of the 8p11-12 region in the case of breast cancer.

Line of anaplastic thyroid cancer: 8p12 in this study.

Line of breast cancer: 8p12 as reported in Garcia, M. J., et al., Oncogene, 24, 5235-5245, 2005; and Line of lung cancer: 8p12 as reported in Tonon, G., et al., Proc. Natl. Acad. Sci. U.S.A. 102, 9625-9635, 2005.

D: The mRNA expression levels of 5 transcriptional products existing in the 8p12 region of 14 types of anaplastic thyroid cancer cell line, as determined by RT-PCR are shown. The expression levels of MGC1136 (NATA1) and RNF122 correlate with the copy numbers thereof. Copy number was determined by FISH experiments using BAC RP11-107B2 as a probe.

A: The results of colony formation assay conducted for KTA1, KTA3, and TTA1 cells expressing the NATA1 gene at low levels are shown. 2 weeks after transfection, the thus generated drug-resistant colonies were selected. Introduction of the NATA1-expressing vector resulted in the production of greater numbers of colonies than that in the case of the empty vector.

B: Quantitative analysis of colony formation is shown. Colonies with sizes greater than 2 mm were counted in 3 separate experiments. The results are shown as mean values thereof.

C: Suppression of NATA1 mRNA expression by NATA1-specific siRNA in 8305C, 8505C, and HTC/C3 cells strongly expressing the NATA1 gene is shown. RT-PCR was performed at 48 hours after transfection.

D: The effects of NATA1-specific siRNA in proliferation of 8305C, 8505C, and HTC/C3 cells as determined by cell proliferation tests are shown.

E: The effects of NATA1-specific siRNA on the numbers of 8305C and 8505C cells that had survived at 72 hours after transfection are shown.

F: The effects of NATA1-specific siRNA on the numbers of 8305C and 8505C cells that had died at 72 hours after transfection are shown. The cells were directly subjected to determination using a trypan blue staining method.

BEST MODES FOR CARRYING OUT THE INVENTION

Hereafter, the present invention is described in detail.

(1) Method for Detecting Cancer

The method for detecting cancer according to the present invention comprises detecting canceration in a specimen using as an indicator the amplification of a gene of the p12 region of chromosome 8 of the specimen.

As a result of the human genome project, transcriptional products (NATA1, MGC1136, MGC2627, MKP8, SKRP3, and dual specificity phosphatase 26: NM_024025) of the human NATA1 gene (other names: MGC1136, MGC2627, MKP8, SKRP3, dual specificity phosphatase 26, and the like) are already known. The human NATA1 gene is located on chromosome 8p12 (Vasudevan, S. A., et al., Biochem. Biophys. Res. Commun. 330, 511-518, 2005). Protein encoded by the human NATA1 gene contains a dual-specificity phosphatase domain and possesses dephosphorylation activity. However, the fact that the human NATA1 gene is an important oncogene involved in the onset of human anaplastic thyroid cancer was unknown before the present invention.

Similarly, the FUT10 gene, the LOC84549 gene, the FLJ23263 gene, and the RNF122 gene are known as genes existing on chromosome 8p12. These genes have each been registered with the National Center for Biotechnology Information (NCBI) database as follows.

FUT10 gene: fucosyltransferase 10 (alpha (1, 3) fucosyltransferase), NM_032664 (REF SEQ ID)

LOC84549 gene: RNA binding motif protein 131, MAK16-like protein RBM13 (RNA binding motif protein 13) (NNP78), NM_032509 (REF SEQ ID)

FLJ23263 gene: C8ORF41, chromosome 8 open reading frame 41, NM_025115 (REF SEQ ID)

RNF122 gene: ring finger protein 122, NM_024787 (REF SEQ ID)

In the human genome, these genes are contained in RP-11 clone ID Nos. 722E23 and 107B2 (available for information purposes at the UCSC genome browser).

As described above, an example of the method for detecting cancer of the present invention is a method that comprises detecting the amplification of the human NATA1 gene in thyroid cells. Appropriate thyroid cells for the detection of the amplification of the human NATA1 gene include tissue cells biopsied from specimen donors. The tissue cells to be used as specimens may be either thyroid cells of a healthy subject or cancer tissue cells of a thyroid cancer patient. Realistically, such tissue cells to be used herein are cells derived from diseased thyroid tissue of a lesion suspected to be undergoing canceration as confirmed by a test or the like or cells derived from thyroid cancer. Possible major subject cells include those derived from thyroid cancer tissues and the like for which determination of the malignancy or the stage progression thereof is required.

When the amplification of the human NATA1 gene is confirmed in "diseased thyroid tissue of a lesion suspected to be undergoing canceration as confirmed by a test or the like," it is revealed that the diseased tissue is undergoing a process toward canceration or is already in the state of canceration and that the malignancy thereof is increasing. Thus, the need to carry out immediate full-scale treatment (e.g., lesion removal by operation or the like or full-scale chemotherapy) is demonstrated. Furthermore, when the amplification of the human NATA1 gene is confirmed in "tissue that is confirmed to be of thyroid cancer and for which determination of the malignancy or the stage progression thereof is required" it is revealed that the malignancy of the cancer tissue is increasing. Hence, the need to carry out immediate full-scale treatment (e.g., lesion removal by operation or the like or full-scale chemotherapy) is demonstrated. A thyroid cell tissue sampled as a specimen can be subjected to the detection method after necessary treatment such as with the preparation of DNA or RNA from the sampled tissue.

In the present invention, as described above, canceration of thyroid cells can be specified by detecting the amplification of the human NATA1 gene in the thyroid cells.

In the present invention, canceration of a specimen is detected using as an indicator the amplification of a gene of the p12 region of chromosome 8 of the specimen. Types of cancer to be detected are not particularly limited, as long as they exhibit the amplification of a relevant gene of the p12 region of chromosome 8. Specific examples of cancer include, but are not limited to, malignant melanoma, malignant lymphoma, lung cancer, esophageal cancer, gastric cancer, large-bowel cancer, rectal cancer, colon cancer, urinary tract tumor, gallbladder cancer, bile duct cancer, biliary tract cancer, breast cancer, liver cancer, pancreatic cancer, testis tumor, maxillary cancer, tongue cancer, lip cancer, oral cavity cancer, pharynx cancer, larynx cancer, ovarian cancer, uterine cancer, prostate cancer, thyroid cancer, brain tumor, Kaposi's sarcoma, angioma, leukemia, polycythemia vera, neuroblastoma, retinoblastoma, myeloma, bladder tumor, sarcoma, osteosarcoma, myosarcoma, skin cancer, basal-cell carcinoma, cutaneous appendage tumor, skin metastatic cancer, and skin melanoma. In the present invention, it is particularly preferable to detect anaplastic thyroid cancer among the above cancer types.

Examples of genes of the p12 region of chromosome 8 that may be used as indicators for amplification in the method of the present invention include the FUT10 gene, the LOC84549 gene, the FLJ23263 gene, the RNF122 gene, and the NATA1 gene. In the method of the present invention, when any one of the above genes is amplified to a level 1.5 or more, preferably 2 or more, further preferably 3 or more, and particularly preferably 5 or more times that of a normal specimen, this can be interpreted as indicating canceration of the specimen.

Examples of typical methods for directly detecting the amplification of a gene of the p12 region of chromosome 8 such as the human NATA 1 gene include the CGH (Comparative Genomic Hybridization) and FISH (Fluorescence in situ Hybridization) methods. According to the detection method of this embodiment, human-NATA1-gene-containing BAC (Bacterial Artificial Chromosome) DNA, YAC (Yeast Artificial Chromosome) DNA, and PAC (P1-derived Artificial Chromosome) DNA (hereinafter, also referred to as BAC DNA or the like) are labeled and then FISH is carried out. Thus, amplified portions of the human NATA1 gene can be detected. Specific examples of BAC DNA containing the human NATA1 gene include RP11-2I13, RP11-14307, RP11-1081G18, RP11-10D7, RP11-107B2, RP11-539P2, and RP11-2I13.

It is appropriate and realistic to carry out the method of the above embodiment using genomic DNA-immobilized substrates.

In general, BAC DNA or the like is obtained in small amounts, which are insufficient to produce a large number of genomic DNA-immobilized substrates that may be put to practical use. Hence, there is a need to obtain such DNA as a gene amplification product (the relevant gene amplification process is also referred to as "inexhaustible supply of a target gene". To realize an inexhaustible supply of a target gene, first, BAC DNA or the like is digested with 4-nucleotide-recognizing enzymes such as Rsa I, Dpn I, and Hae III and then an adaptor is added to perform ligation. Such an adaptor is an oligonucleotide comprising 10 to 30 nucleotides and preferably 15 to 25 nucleotides and the double strand has a complementary sequence. Hence, after annealing, the 3'-terminal oligonucleotide on the side at which a blunt end is formed should be phosphorylated. Next, amplification is carried out by the PCR (Polymerase Chain Reaction) method using a primer having a sequence identical to that of one of the oligonucleotides of an adaptor. Hence, an inexhaustible supply of a target gene can be realized. Meanwhile, a 50- to 70-nucleotide-long aminated oligonucleotide that is characteristic in all BAC DNAs can also be used as a probe for detection.

The thus obtained BAC DNAs or the like (of which inexhaustible supplies have been realized) are immobilized on a substrate, and preferably on a solid substrate, so that a desired DNA-immobilized substrate can be produced. A glass plate is preferable as a solid substrate. In the case of a solid substrate such as a glass plate, it is more preferable to coat such a substrate via cohesion of poly-L-lysine, aminosilane, gold, aluminum, or the like.

The above DNAs (of which inexhaustible supplies have been realized) are spotted onto the substrate at a concentration preferably ranging from 10 µg/µl to 5 µg/µl and more preferably ranging from 1 ng/µl to 200 ng/µl. The amount of such DNA to be spotted preferably ranges from 1 nl to 1 µl and more preferably from 10 nl to 100 nl. Furthermore, the sizes and shapes of the spots to be applied to the substrate are not particularly limited. For example, a spot can have a diameter ranging from 0.01 mm to 1 mm, and the shape viewed from above can be circular or elliptic. The thickness of a dry spot is not particularly limited and can range from 1 µm to 100 µm. Moreover, the number of such spots is not particularly limited and can range from 10 to 50,000 and more preferably from 100 to 5,000 spots per base used herein. The number of times that each DNA is spotted ranges from one to four. It is preferable to spot each DNA two or three times.

Dry spots can be prepared by spotting BAC DNA or the like (of which inexhaustible supplies have been realized) on a substrate using a spotter, forming a plurality of spots, and then drying the spots, for example. An inkjet printer, a pin array printer, or a bubble jet (trademark) printer can be used as a spotter. The use of an inkjet printer is desirable. For example, GENESHOT (NGK Insulators, Ltd., Nagoya) or the like can be used.

The thus obtained BAC DNA or the like (of which inexhaustible supplies have been realized) is immobilized on a base, and preferably a solid base, so that a desired DNA-immobilized base can be produced.

Furthermore, an example of a means for directly detecting the amplification of the human NATA1 gene is a Southern blot method. The Southern blot method comprises separating and immobilizing the genomic DNA obtained from a specimen and detecting hybridization between the DNA and the human NATA1 gene, so as to detect the presence of the gene in the specimen.

Furthermore, the amplification of the human NATA1 gene can also be detected by the Northern blot method or the real-time RT-PCR method. The Northern blot method comprises separating and immobilizing mRNA obtained from a specimen and detecting hybridization between the mRNA and the human NATA1 gene, so as to detect the presence of the mRNA of the gene in the specimen. The real-time RT-PCR method is a method for determining (in realtime) the amplification of a target gene as a result of a reverse transcription reaction and a polymerase chain reaction. By such method, mRNA serving as a template can be quantified based on amplification rate. The quantification is carried out using a fluorescent dye. There are 2 methods that may be used for the quantification. Specifically, a method involving specific insertion (intercalation) of a dye (e.g., SYBR green) emitting fluorescence into double-stranded DNA and a method involving a probe prepared by binding a fluorescent dye to an oligonucleotide specific to a DNA sequence to be amplified are known.

(2) Method for Suppressing Cell Proliferation and Cell Proliferation Suppressing Agent According to the present invention, a method for suppressing cell proliferation, which comprises in vitro introduction of siRNA, shRNA, or an antisense oligonucleotide of a gene selected from the group consisting of the FUT10 gene, LOC84549 gene, the FLJ23263 gene, the RNF122 gene, and the NATA1 gene into cancer cells, and a cell proliferation suppressing agent comprising the above siRNA, shRNA, or antisense oligonucleotide are provided.

siRNA is a double-stranded RNA with a length of approximately 20 (e.g., approximately 21 to 23 nucleotides) or fewer nucleotides. Through expression of such siRNA in cells, the expression of a gene (in the present invention, the FUT10 gene, the LOC84549 gene, the FLJ23263 gene, the RNF122 gene, or the NATA1 gene) that is a target of such siRNA can be suppressed.

siRNA that is used in the present invention may be in any form, as long as it can induce RNAi. Here, the term "siRNA" is an abbreviation for "short interfering RNA." siRNA is a short-chain double-stranded RNA of 10 or more base pairs, which is produced by artificial chemical synthesis, biochemical synthesis, in vivo synthesis, or in vivo degradation of double-stranded RNA of approximately 40 or more nucleotides. In general, siRNA has a structure comprising 5'-phosphoric acid and 3'-OH, where the 3' terminus projects by approximately 2 nucleotides. RISC (RNA-induced-silencing-complex) is formed through the binding of a protein (specific to the siRNA) to siRNA. This complex recognizes and binds to mRNA having a sequence identical to that of siRNA. The mRNA is cleaved at the central part of siRNA via RNaseIII-like enzyme activity.

It is preferable that an siRNA sequence and a mRNA sequence to be cleaved as a target match 100%. However, such 100% match is not always required, when unmatched nucleotides are located in a position(s) other than the central part of the siRNA. This is because partial cleavage activity due to RNAi often remains.

Preferably, a homologous region (between the nucleotide sequence of siRNA and the nucleotide sequence of the FUT10 gene, the LOC84549 gene, the FLJ23263 gene, the RNF122 gene, or the NATA1 gene, the expression of which is to be suppressed) does not contain a translation initiation region of the relevant gene. This is because various transcription factors and translation factors are predicted to bind to such translation initiation region. Specifically, it is predicted that siRNA would thus be unable to effectively bind to mRNA, resulting in lower effectiveness. Accordingly, a sequence having homology is preferably located 20 nucleotides and more preferably 70 nucleotides away from the translation initiation region of the gene. An example of a sequence having homology is a sequence in the vicinity of the 3' terminus of the gene.

According to another embodiment of the present invention, shRNA (short hairpin RNA) comprising a short hairpin structure having a projection at the 3' terminus can be used as a factor capable of suppressing the expression of a target gene via RNAi. "shRNA" means a molecule of approximately 20 or more base pairs, which is formed when a single-stranded RNA contains partially palindromic nucleotide sequences so that it forms a double-stranded structure within the molecule leading to the formation of a hairpin-like structure. When such shRNA is introduced into a cell, shRNA is degraded to a length of approximately 20 nucleotides (typically 21 nucleotides, 22 nucleotides, or 23 nucleotides, for example) within the cell. Hence, shRNA can induce RNAi in a manner similar to that in the case of siRNA. As described above, since shRNA can induce RNAi in a manner similar to the case of siRNA, shRNA can be effectively used in the present invention.

Preferably, shRNA has a projecting 3' terminus. The length of a double-stranded portion is not particularly limited and is preferably approximately 10 or more nucleotides and more preferably approximately 20 or more nucleotides. Here, the projecting 3' terminus is preferably a DNA, more preferably a DNA of at least 2 or more nucleotides, and further preferably a DNA of 2 to 4 nucleotides.

As described above, in the present invention, siRNA or shRNA can be used as a factor capable of suppressing the expression of the FUT10 gene, the LOC84549 gene, the FLJ23263 gene, the RNF122 gene, or the NATA1 gene via RNAi. Examples of advantages of siRNA include (1) high safety (RNA itself is not incorporated into a chromosome of a normal cell when it is introduced into the cell, so that treatment using the RNA does not cause any inheritable mutations) and (2) stability (short-chain double-stranded RNA can be chemically synthesized relatively easily and such double-stranded RNA is stable). Another example of an advantage of shRNA is that when treatment is performed through long-term suppression of gene expression, a vector capable of transcribing shRNA within cells can be prepared and then introduced into the cells.

siRNA or shRNA that is used in the present invention and can suppress the expression of the FUT10 gene, the LOC84549 gene, the FLJ23263 gene, the RNF122 gene, or the NATA1 gene via RNAi may be artificially and chemically synthesized. siRNA or shRNA can also be prepared through in vitro RNA synthesis using DNA with a hairpin structure wherein a sense strand DNA sequence and an antisense strand DNA sequence are linked in a reversible manner and T7 RNA polymerase. In the case of in vitro synthesis, antisense and sense RNAs can be synthesized using T7 RNA polymerase, a T7 promoter, and a template DNA. After in vitro annealing thereof, the resultant is introduced into cells. RNAi is thus induced and the expression of a target gene is suppressed. For example, such RNA can be introduced into cells by a calcium phosphate method or using various transfection reagents (e.g., oligofectamine, lipofectamine, and lipofection).

The above siRNA or shRNA is useful as a cell proliferation suppressing agent. Examples of the route of administration of the cell proliferation suppressing agent of the present invention include oral administration, parenteral administration (e.g., intravenous administration, intramuscular administration, subcutaneous administration, intradermal administration, transmucosal administration, intrarectal administration, intravaginal administration, local administration to affected area, and skin administration) and direct administration to affected area. When the agent of the present invention is used as a pharmaceutical composition, a pharmaceutically acceptable additive can be compounded with the agent, if necessary. Specific examples of such pharmaceutically acceptable additive include, but are not limited to, antioxidants, preservatives, coloring agents, flavoring agents, diluents, emulsifiers, suspending agents, solvents, fillers, extending agents, buffer agents, delivery vehicles, diluents, carriers, excipients, and/or pharmaceutical adjuvants.

Examples of the form of the pharmaceutical preparation of the agent of the present invention are not particularly limited and include liquids, injections, and sustained release agents. A solvent that is used for prescribing the agent of the present invention as the above form of the pharmaceutical preparation may be either aqueous or non-aqueous.

Furthermore, siRNA or shRNA that is an active ingredient of the cell proliferation suppressing agent of the present invention can be administered in the form of a non-viral or viral vector. In the case of a non-viral vector form, a method that involves introducing a nucleic acid molecule using a liposome (e.g., a liposome method, an HVJ-liposome method, a cationic liposome method, a lipofection method, and a lipofectamine method), a microinjection method, a method that involves transferring a nucleic acid molecule together with a carrier (metal particles) into cells using a gene gun, or the like can be employed. When siRNA or shRNA is administered to a living body using a viral vector, viral vectors such as a recombinant adenovirus vector or a retrovirus vector can be used. A gene can be introduced into cells or tissues by introducing DNA expressing siRNA or shRNA into detoxified DNA or RNA viruses such as retroviruses, adenoviruses, adeno-associated viruses, herpesviruses, vaccinia viruses, poxviruses, polioviruses, Sindbis viruses, Sendai viruses, or SV40 viruses and then infecting the cells or tissues with such recombinant viruses.

The dose of the cell proliferation suppressing agent of the present invention can be determined by persons skilled in the art in view of purposes of use, disease severity, patient age, body weight, sex, and past medical history, or types of siRNA or shRNA that are active ingredients. The dose of siRNA or shRNA is not particularly limited and ranges from approximately 0.1 ng to approximately 100 mg/kg/day and preferably from approximately 1 ng to approximately 10 mg/kg/day. The effect of RNAi is generally observable for 1 to 3 days after administration. Therefore, administration is preferably performed at a frequency of once a day to once every 3 days. When an expression vector is used, administration of siRNA or shRNA can be performed approximately once a week.

In the present invention, an antisense oligonucleotide can also be used as a cell proliferation suppressing agent. Antisense oligonucleotides to be used in the present invention are nucleotides that are complementary or hybridize to sequences of 5 to 100 nucleotides within the DNA sequence of the FUT10 gene, the LOC84549 gene, the FLJ23263 gene, the RNF122 gene, or the NATA1 gene. Such an antisense oligonucleotide may be either DNA or RNA or may be modified as long as its functions remain untouched. Examples of an "antisense oligonucleotide" in this description include not only an oligonucleotide wherein all nucleotides corresponding to nucleotides composing a predetermined DNA or mRNA region are complementary to their counterparts, but also an oligonucleotide that contains some mismatching nucleotides, as long as such oligonucleotides can stably hybridize to DNA or mRNA.

In addition, such antisense oligonucleotide may be modified. After appropriate modification of such antisense oligonucleotide, the resulting modified antisense oligonucleotide will be degraded with difficulty in vivo. This enables more stable inhibition of ITIIα. Examples of such modified oligonucleotide include S-oligo type (phosphorothioate-type), C-5 thyazole type, D-oligo type (phosphodiester-type), M-oligo type (methylphosphonate-type), peptide nucleic acid type, phosphodiester binding type, C-5 propinyl pyrimidine type, 2-O-propylribose, and 2'-methoxyribose type antisense oligonucleotides. Moreover, such antisense oligonucleotide may also be an antisense oligonucleotide wherein at least some of the oxygen atoms composing phosphate groups are substituted with sulfur atoms or otherwise modified. Such antisense oligonucleotide is particularly excellent in terms of nuclease resistance, water solubility, and affinity for RNA. An example of an antisense oligonucleotide wherein at least some of the oxygen atoms composing phosphate groups are substituted with sulfur atoms or otherwise modified is an S-oligo type oligonucleotide.

The number of nucleotides in such antisense oligonucleotide is preferably 50 or less and more preferably 25 or less. Too large a number of nucleotides results in increased effort and cost in oligonucleotide synthesis and lowered yields. Furthermore, the number of nucleotides of such antisense oligonucleotide is 5 or more and preferably 9 or more. A number of nucleotides of 4 or less is undesirable because of the resulting lowered specificity to a target gene.

Such antisense oligonucleotide (or a derivative thereof) can be synthesized by a standard method. For example, an antisense oligonucleotide or a derivative thereof can be easily synthesized using a commercially available DNA synthesizer (e.g., one produced by Applied Biosystems). It can be obtained by a synthesis method such as a solid-phase synthesis method using phosphoroamidite or a solid-phase synthesis method using hydrogen phosphonate.

When an antisense oligonucleotide is used as a cell proliferation suppressing agent in the present invention, it is generally provided in the form of a pharmaceutical composition containing the antisense oligonucleotide and an additive for pharmaceutical preparation (e.g., a carrier or an excipient). The antisense oligonucleotide can be administered as a medicament to mammals, with examples thereof including humans. The route of administration for such antisense oligonucleotide is not particularly limited and may be oral administration or parenteral administration (e.g., intramuscular administration, intravenous administration, subcutaneous administration, peritoneal administration, transmucosal administration in the nasal cavity or the like, and inhalation administration).

The form of the pharmaceutical preparation of such antisense oligonucleotide is not particularly limited. Examples of pharmaceutical preparations for oral administration include tablets, capsules, granules, powders, fine granules, liquids, and syrups. Examples of pharmaceutical preparations for parenteral administration include injections, infusions, suppositories, inhalants, transmucosal absorption systems, transdermal absorption systems, nasal drops, and ear drops. The form of a drug containing the antisense oligonucleotide, an additive to be used for a relevant pharmaceutical preparation, a method for producing such a pharmaceutical preparation, and the like can be appropriately selected by persons skilled in the art.

The dose of the antisense oligonucleotide can be appropriately selected through comprehensive consideration of patient sex, age, or body weight, symptom severity, purpose of administration (e.g., prevention or treatment), or the presence or the absence of other complicating symptoms. The dose generally ranges from 0.1 μg/kg body weight/day to 100 mg/kg body weight/day and preferably ranges from 0.1 μg/kg body weight/day to 10 mg/kg body weight/day.

(3) Method for Activating Cell Proliferation and a Cell Proliferation Activating Agent According to the present invention, a method for activating cell proliferation, which comprises in vitro introduction of a gene selected from the group consisting of the FUT10 gene, the LOC84549 gene, the FLJ23263 gene, the RNF122 gene, and the NATA1 gene into cells and a cell proliferation activating agent containing the above gene are provided.

The gene selected from the group consisting of the FUT10 gene, the LOC84549 gene, the FLJ23263 gene, the RNF122 gene, and the NATA1 gene can be used in the form of a recombinant vector incorporating the gene. Examples of vectors that are used herein include viral vectors and vectors for expression in animal cells. Preferably, viral vectors may be used. Examples of viral vectors include retroviral vectors, adenovirus vectors, adeno-associated viral vectors, baculovirus vectors, vaccinia virus vectors, and lentiviral vectors. As vectors for expression in animal cells, pCXN2 (Gene, 108, 193-200, 1991), PAGE207 (JP Patent Publication (Kokai) No. 6-46841 A (1994)), and altered products thereof can be used, for example.

The above recombinant vector can be produced by introducing the vector into an appropriate host for transformation and then culturing the thus obtained transformant. When a recombinant vector is a viral vector, animal cells capable of producing viruses are used as hosts into which such vector is introduced. Examples of such animal cells include COS-7 cells, CHO cells, BALB/3T3 cells, and HeLa cells. Examples of hosts to be used for retroviral vectors include ΨCRE, ΨCRIP, and MLV. Examples of hosts to be used for adenoviral vectors or adeno-associated viral vectors include 293 cells derived from human fetal kidney. Viral vectors can be introduced into animal cells via a calcium phosphate method or the like. Furthermore, when a recombinant vector is a vector for expression in animal cells, examples of hosts that can be used for introduction of such vector include those of the *Escherichia coli* K12 strain, the HB 101 strain, and the DH 5α strain. Transformation of *Escherichia coli* is known by persons skilled in the art.

The thus obtained transformants are each cultured in an adequate medium under adequate culture conditions. For instance, a transformant of *Escherichia coli* can be cultured using a liquid medium with a pH approximately between 5 and 8 containing carbon sources, nitrogen sources, inorganic matter, and the like, which are necessary for cell growth. In general, culture is carried out at 15° C. to 43° C. for approximately 8 to 24 hours. In such case, a target recombinant vector can be obtained after the termination of culture via general DNA isolation and purification methods.

Furthermore, transformants of animal cells can be cultured using a medium such as a 199 medium, an MEM medium, or a DMEM medium containing approximately 5% to 20% of fetal calf serum. The pH of such medium is preferably approximately between 6 and 8. In general, culture is carried out at approximately 30° C. to 40° C. for approximately 18 to 60 hours. In such case, since viral particles containing a target recombinant vector are released into a culture supernatant, the target recombinant vector can be obtained as a result of concentration and purification of viral particles via a cesium chloride centrifugation method, a polyethylene glycol precipitation method, a filter concentration method, or the like.

The cell proliferation activating agent of the present invention can be produced by compounding the above gene as an active ingredient with a base that is generally used as a gene therapeutic agent. Moreover, when the above gene is incorporated into a viral vector, viral particles containing a recombinant vector are prepared and the viral particles are compounded with a base that is generally used as a gene therapeutic agent.

As the above base, a base generally used for an injection can be used. Examples thereof include distilled water, a salt solution containing sodium chloride, a mixture of sodium chloride and an inorganic salt, or the like, a solution of mannitol, lactose, dextran, glucose, or the like, an amino acid solution of glycine, arginine, or the like, and a mixed solution of an organic acid or salt solution and a glucose solution. Alternatively, in accordance with conventional techniques known by persons skilled in the art, an injection can be prepared as a solution, suspension, or dispersion using an adjuvant such as an osmoregulator, a pH adjuster, a plant oil, or a surfactant with the above base. Such injection can also be prepared as a pharmaceutical preparation that is solubilized at the time of use through operations such as pulverization and freeze drying.

The route of administration of the cell proliferation activating agent of the present invention may be a form of general systemic administration such as intravenous administration or intraarterial administration, or a form of local administration such as local injection or oral administration. Furthermore, administration of the cell proliferation activating agent can also be performed through a combination of catheterization, a gene transfer technique, or surgical operation.

The dose of the cell proliferation activating agent of the present invention varies depending on patient age, sex, and symptoms, the route of administration, the number of doses, and dosage forms. In general, the daily dose (in terms of weight of recombinant gene) ranges from 1 μ/kg body weight to 1000 mg/kg body weight for an adult. Preferably, it ranges from 10 μg/kg body weight to 100 mg/kg body weight. The number of doses administered is not particularly limited.

EXAMPLES

Example 1

Amplification of Human 8p12 Region in Anaplastic Thyroid Cancer Cells

To detect novel gene amplification in anaplastic thyroid cancer, genomic DNAs prepared from 14 types of anaplastic thyroid cancer cells were subjected to CGH array analysis using a CGH array (MGC Cancer Array-800).

In addition, the genomic DNA of a healthy male subject was labeled with Cy5 as a control. Genomic DNAs prepared from the above anaplastic thyroid cancer cells were used as test DNAs and labeled with Cy3. Specifically, each genomic DNA (0.5 μg) digested with DpnII was labeled using a BioPrime Array CGH Genomic Labeling System (Invitrogen) in the presence of 0.6 mM dATP, 0.6 mM dTTP, 0.6 mM dGTP, 0.3 mM dCTP, 0.3 mM Cy3-dCTP (anaplastic thyroid cancer cells), or 0.3 mM Cy5-dCTP (normal cells). Cy3- and Cy5-labeled dCTPs were obtained from Amersham Biosciences. Ethanol was added so that the genomic DNA labeled with Cy3 or Cy5 was precipitated in the presence of Cot-1 DNA (Invitrogen). The resultant was dissolved in 120 μl of a hybridization mixture (50% formamide, 10% Dextran sulfate, 2×SSC (1×SSC: 150 mM NaCl/15 mM Sodium Citrate), 4% sodium dodecyl sulfate, pH 7.0). After 30 minutes of incubation at 37° C., the resultant was introduced onto a CGH array set in a hybridization chamber. Incubation took place for 48 to 72 hours while shaking was carried out at a speed of 3 rpm (round per minute) at 37° C. Subsequently, the CGH array was washed in a 50% formamide/2×SSC (pH 7.0) solution at 50° C. for 15 minutes and then washed at 50° C. for 15 minutes in 2×SSC/0.1% SDS. After air-drying, the CGH array was monitored for fluorescence derived from Cy3 and Cy5 using GenePix 4000B scanner (Axon Instruments, CA, U.S.A.). The thus obtained results were analyzed using a GenePix Pro 4.1 imaging software (Axon Instruments, CA, U.S.A.). The average fluorescence intensity derived from Cy3 was adjusted to be the same as that of fluorescence intensity derived from Cy5, thereby allowing the ratio of Cy3 to Cy5 to be found. When a genome has no abnormality, the resulting ratio is 1:1 (log 2 ratio=0). Determination was performed as follows. A ratio of 1.32 (or higher): 1 (log 2 ratio=0.4 or more) indicates the presence of genome amplification and a ratio of 4 (or higher) 1 indicates the confirmation of significant amplification. A ratio of 0.75 (or lower) 1 (log 2 ratio=−0.4 or less) indicates possible heterozygote deletion in the genome and a ratio of 0.25 (or lower): 1 (log 2 ratio=−2 or less) indicates an extremely high possibility of homozygote deletion in the genome.

Figure 1:
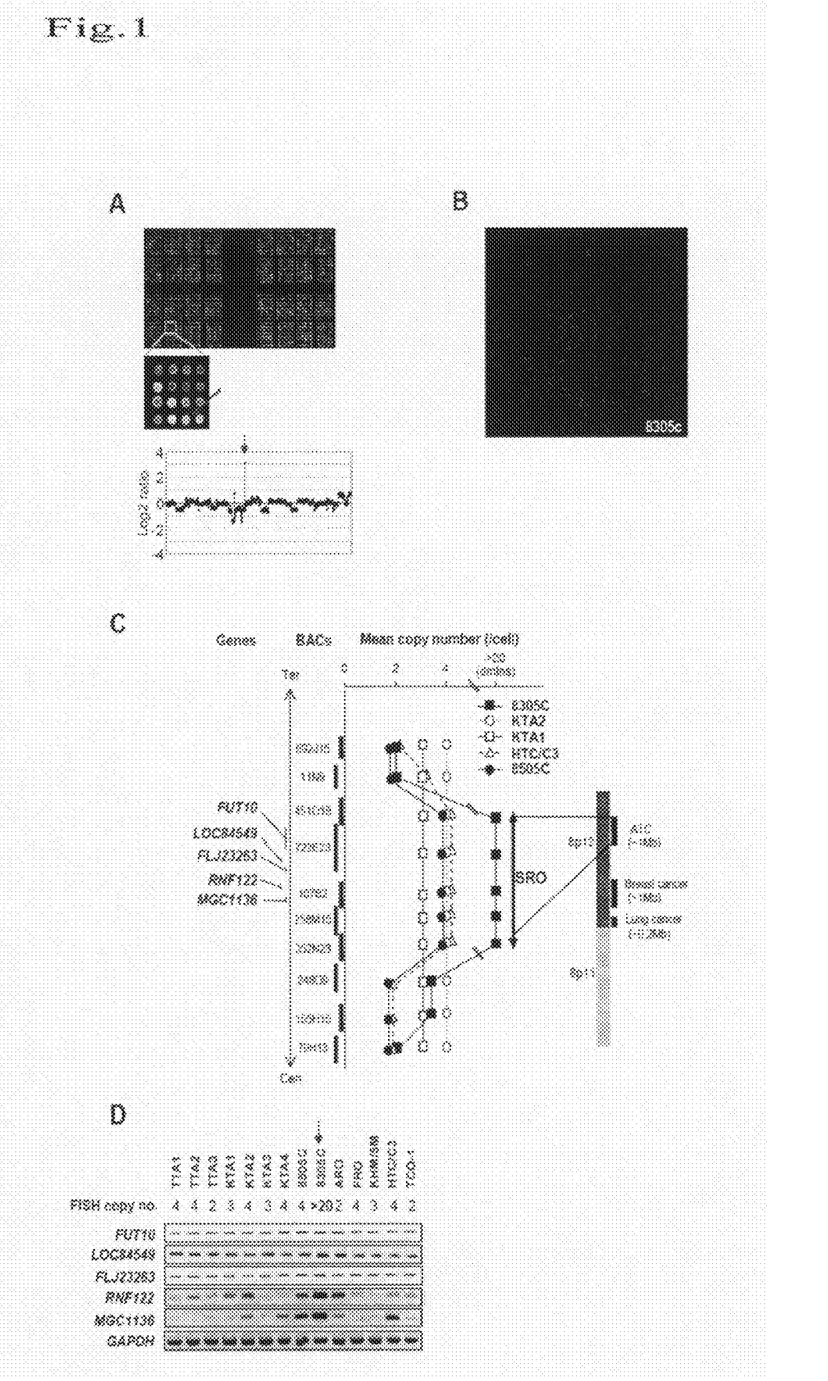
FIG. 1 shows the amplification and overexpression of NATA1 in the anaplastic thyroid cancer cell lines.

As a result, amplification (log 2 ratio>2) was confirmed in 6 clones/gene (Table 1). 5 clones/gene (MET, MYC, PVT1, YAP1, and CIAP1) of these clones had already been reported in various types of human cancer. However, in the case of anaplastic thyroid cancer (8305C) cells, amplification of PAC clone RP1-25D10 existing on chromosome 8p12 was discovered. The log 2 ratio in this case was 3.2. (FIG. 1A: a typical array image obtained by subjecting the genomic DNA of 8305C (test cells) to CGH analysis on the CGH array described in these examples. Amplification of copy number on chromosome 8p12 is denoted with a clear signal.)

TABLE 1

Gene amplification or homozygous deletion in 14 types of anaplastic thyroid cancer cell lines as detected by the CGH array method

| Changes | Gene | Locus | No. |
|---|---|---|---|
| High-level amplification (log2 ratio >2.0) | MET | 7q31 | 1 |
| | NATA1 | 8p12 | 1 |
| | MYC | 8q24 | 2 |
| | PVT1 | 8q24 | 2 |
| | YAP1 | 11q22.1 | 1 |
| | CIAP1 | 11q22 | 1 |
| Homozygous deletion (log2 ratio <−2.0) | MLLT3 | 9p22 | 1 |
| | P16 | 9p21 | 4 |

Furthermore, a FISH method was performed for anaplastic thyroid cancer cells (8305C, 8505C, KTA1, KTA2, and HTC/C3) using as a probe a BAC clone (RP11-258M15) located in the vicinity of RP1-25D10, so as to confirm the amplification of the 8p12 region in 8305C cells. FIG. 1B shows the results. Moreover, FIG. 1C shows the correlation between BAC clones located in the 8p12 region and amplification of copy number as determined by the FISH method.

Example 2

Amplification of the Human NATA1 Gene in Anaplastic Thyroid Cancer Cells

To specify which gene was actually amplified in anaplastic thyroid cancer cells, genomic regions that had exhibited a large number of amplified copies as determined by the FISH method were analyzed using the human genome database. Hence, candidate genes were specified. The expression levels of the candidate genes were detected by the RT-PCR method using total RNA actually extracted from anaplastic thyroid cancer cells.

The presence of five candidate genes (FUT10, LOC84549, FLJ23263, RNF122, and NATA1 (MGC1136)) was confirmed in the genomic regions that had exhibited high levels of amplification, as analyzed using the human genome database (FIG. 1C). The expression of the 5 candidate genes was analyzed using total RNAs extracted from 14 types of anaplastic thyroid cancer cells. Thus, overexpression of the NATA1 (MGC1136) gene in particularly the 8305C cell line was revealed (FIG. 1D).

Example 3

Figure 2:
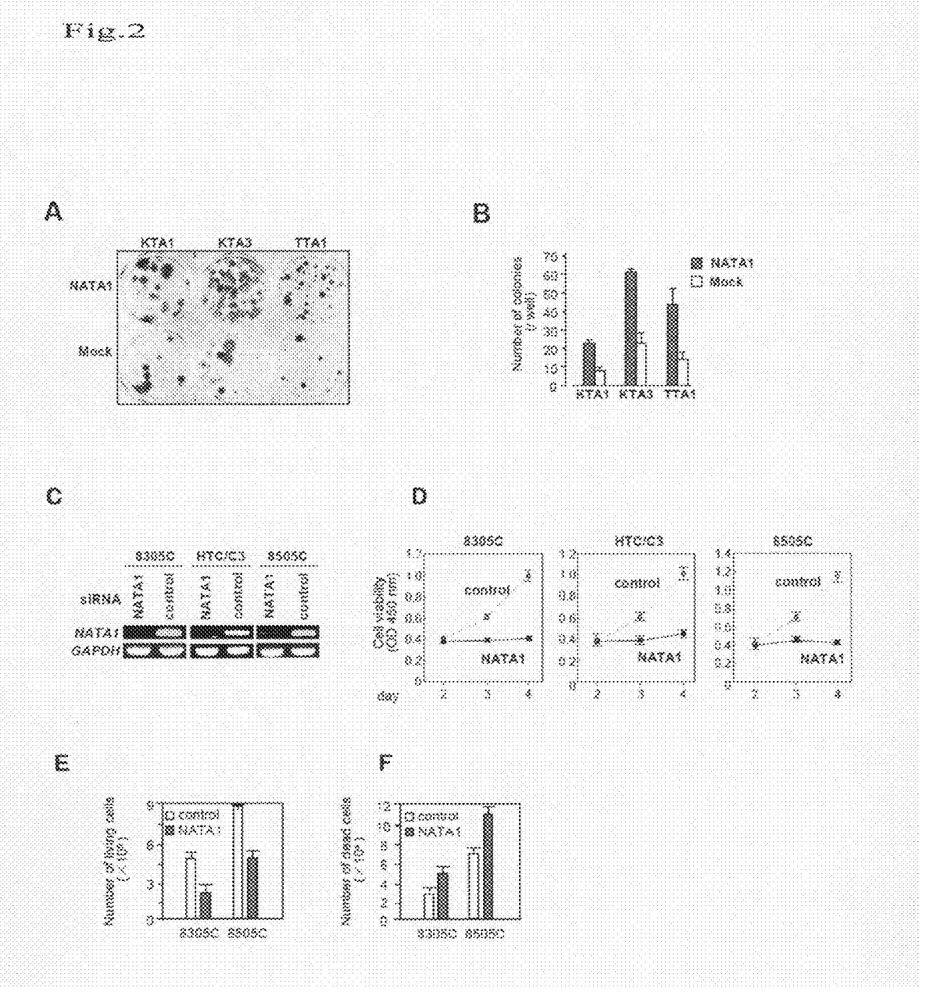
FIG. 2 shows the effect of NATA1 in the proliferation of anaplastic thyroid cancer cells.

Anaplastic Thyroid Cancer Cell Proliferation Due to the Expression of the Human NATA1 Gene To clarify the role of the human NATA1 gene in canceration of thyroid anaplastic cells, whether or not the cell proliferation of anaplastic thyroid cancer cell lines had been activated when the gene had been over-expressed was examined. First, a plasmid (pCMV-Tag 3B-NATA1) expressing an myc tag of the human NATA1 gene was constructed. This plasmid was prepared by inserting the human NATA1 gene (cDNA-amplified by RT-PCR) into a pCMV-Tag 3 expression vector (Stratagene), so that the myc epitope matched the translation frame. An empty vector (pCMV-Tag 3B-mock) into which the human NATA1 gene had not been inserted was used as a control. These expression vectors were mixed with FuGENE6 (Roche Diagnostics) serving as a transfection reagent and then transfected into KTA1, KTA3, and TTA1 cells. 3 weeks later, cells that had proliferated in the presence of a neomycin drug G418 were fixed with 70% ethanol and then stained with crystal violet. The number of colonies was then determined. As a result, it was found that in the cases of cells into which the vector expressing the human NATA1 gene had been transfected, the number of colonies had been significantly amplified. ((FIG. 2A: The genes were transfected into KTA1, KTA3, and TTA1 cells using the NATA1-expressing vector pCMV-Tag 3B-NATA1 and the empty vector pCMV-Tag 3B-mock. Introduction of the human NATA1 gene resulted in a significantly increased number of colonies formed. (B): The results of determining the number of colonies generated in the cases of KTA1, KTA3, and TTA1 cells are shown. The number of colonies formed in the experiment in FIG. 2A above was determined and the results were presented in a bar graph. Colonies with sizes greater than 2 mm were counted. The experiment was conducted 3 times. The results are each shown as mean value±SE.) These results clearly indicate that the expression of the human NATA1 gene activates the growth of anaplastic thyroid cancer. The human NATA1 gene is inferred to function as an oncogene.

Example 4

Suppression of the Proliferation of Anaplastic Thyroid Cancer Cells by Inactivation of the Human NATA1 Gene Based on the results in Example 3, it was now examined whether or not suppression of the expression of the NATA1 gene suppressed the proliferation of anaplastic thyroid cancer cells. First, small interfering RNA (siRNA) of the human NATA1 gene was synthesized. siRNA of the NATA1 gene was synthesized by Dharmacon Research. The target sequence thereof was CATCCTTTCCTCAATGTCT (SEQ ID NO: 1) (nucleotide sequence 513-531; GenBank accession no. AB158288) in the form of double-stranded RNA. This siRNA was transfected into 8305C, 8505C, and HTC/C3 cells (FIG. 1D) strongly expressing the NATA1 gene using Optifect Reagent (Invitrogen) serving as a transfection reagent. 48 hours later, it was revealed by RT-PCR analysis that NATA1-specific siRNA had caused decreases in the expression levels of the endogenous NATA1 gene in 3 types of cell line, as compared with the case of the control siRNA (FIG. 2E). Furthermore, it is also clear that the NATA1-specific siRNA suppresses cell proliferation (FIG. 2F). Such suppression of cell proliferation was clearly observed when the numbers of 8305C and 8505C cells were determined 72 hours after transfection (FIG. 2G). Furthermore, the cells were stained with trypan blue, so as to confirm whether they were alive or dead. It was thus revealed that more cells into which the NATA1-specific siRNA had been transfected than cells into which the control siRNA had been transfected had died (FIG. 2H). These results clearly demonstrate that the suppression of the expression of the human NATA1 gene can suppress the proliferation of anaplastic thyroid cancer cells and that the human NATA1 gene can function as an cancer suppressing agent.

EFFECT OF THE INVENTION

The present invention has made it possible to precisely understand the classification of cancer types, signs of canceration, cancer stage progression, and malignancy in thyroid cell specimens. Furthermore, proliferation of anaplastic thyroid cancer cells can be suppressed through inhibition of transcriptional products of the NATA1 gene that is amplified in the anaplastic thyroid cancer cells.

The invention claimed is:

1. A method for detecting cancer in a human which comprises detecting canceration of a specimen using the amplification of a NATA 1 gene of the p12 region of human chromosome 8 in the specimen as an indicator, wherein the specimen is a cell derived from the thyroid gland, and the cancer is anaplastic thyroid cancer.

2. The method for detecting cancer according to claim 1 wherein the value indicating the degree of such gene amplification is 1.5 or more times greater than that of a normal specimen.

3. The method for detecting cancer according to claim 1 wherein gene amplification is detected using a DNA chip method, a Southern blot method, a Northern blot method, a real-time RT-PCR method, a FISH method, a CGH method, or an array CGH method.

* * * * *